United States Patent
Kessler

(10) Patent No.: US 9,513,238 B2
(45) Date of Patent: Dec. 6, 2016

(54) METHOD AND DEVICE FOR PERFORMING AN X-RAY FLUORESCENCE ANALYSIS

(71) Applicant: Helmut Fischer GmbH Institut fur Elektronik und Messtechnik, Sindelfingen (DE)

(72) Inventor: Jens Kessler, Stuttgart (DE)

(73) Assignee: Helmut Fischer GmbH Institut für Elektronik und Messtechnik, Sindelfingen (DE)

( * ) Notice: Subject to any disclaimer, the term of this patent is extended or adjusted under 35 U.S.C. 154(b) by 34 days.

(21) Appl. No.: 14/648,264

(22) PCT Filed: Oct. 22, 2013

(86) PCT No.: PCT/EP2013/072001
§ 371 (c)(1),
(2) Date: May 29, 2015

(87) PCT Pub. No.: WO2014/082795
PCT Pub. Date: Jun. 5, 2014

(65) Prior Publication Data
US 2015/0300966 A1    Oct. 22, 2015

(30) Foreign Application Priority Data
Nov. 29, 2012 (DE) .......... 10 2012 111 572

(51) Int. Cl.
*G01N 23/223* (2006.01)

(52) U.S. Cl.
CPC ....... *G01N 23/223* (2013.01); *G01N 2223/076* (2013.01); *G01N 2223/633* (2013.01)

(58) Field of Classification Search
None
See application file for complete search history.

(56) References Cited

U.S. PATENT DOCUMENTS 4,393,512 A * 7/1983 Wang .................. G01N 23/223
378/145

5,406,609 A * 4/1995 Arai ................ B82Y 10/00
378/45

(Continued)

FOREIGN PATENT DOCUMENTS

AT    300 420 B    7/1972
AT    300420 B  *  7/1972 .......... G01N 23/223

(Continued)

OTHER PUBLICATIONS

International Preliminary Report on Patentability for corresponding Application No. PCT/EP2013/072001 dated Jun. 2, 2015.

(Continued)

*Primary Examiner* — Andrew Smyth
(74) *Attorney, Agent, or Firm* — Renner, Otto, Boisselle & Sklar, LLP

(57) ABSTRACT

The invention relates to a method for performing an x-ray fluorescence analysis, in which method a primary radiation (16) is directed at a specimen (12) by an x-radiation source (14) and in which method a secondary radiation (18) emitted by the specimen (12) is detected by a detector (20) and evaluated by means of an evaluating unit (21), wherein at least one filter (23) having at least one filter layer (25) forming a filter plane is brought into the beam path of the secondary radiation (18) and acts as a band-pass filter in dependence on an angle α of the filter layer (25) to the secondary radiation (18) and an interfering wavelength of the secondary radiation (18) is coupled out by Bragg reflection, the angle α of the filter layer (25) of the filter (23) is set by means of a setting apparatus (31) to reflect at least one interfering wavelength of the secondary radiation (18) by Bragg reflection, and the coupled-out wavelength of the secondary radiation (18) is detected by a second detector (32) and the signals determined therefrom are forwarded to the evaluating unit (21).

13 Claims, 1 Drawing Sheet

(56) References Cited

U.S. PATENT DOCUMENTS

| | | | | |
|---|---|---|---|---|
| 5,497,008 | A * | 3/1996 | Kumakhov | B82Y 10/00 250/505.1 |
| 8,781,070 | B2 * | 7/2014 | Wormington | G01N 23/20 378/81 |
| 2003/0048494 | A1 * | 3/2003 | Ayres | G03H 1/04 359/10 |
| 2004/0047446 | A1 * | 3/2004 | Platonov | B82Y 10/00 378/42 |
| 2005/0067581 | A1 * | 3/2005 | Berhke | G01N 23/00 250/395 |
| 2008/0310587 | A1 * | 12/2008 | Hegeman | G01N 23/223 378/44 |
| 2009/0296887 | A1 * | 12/2009 | Boyden | G01T 1/161 378/87 |
| 2011/0058652 | A1 * | 3/2011 | Seidler | B82Y 10/00 378/82 |

FOREIGN PATENT DOCUMENTS

| | | | | |
|---|---|---|---|---|
| DE | WO 9522758 A1 * | 8/1995 | | B82Y 10/00 |
| DE | 44 07 278 A1 | 9/1995 | | |
| DE | 4407278 A1 * | 9/1995 | | B82Y 10/00 |
| DE | 60015346 * | 12/2004 | | B82Y 10/00 |
| DE | 300420 T * | 8/2005 | | D06N 5/00 |
| DE | 600 15 346 T2 | 11/2005 | | |
| DE | 60015346 T2 * | 11/2005 | | B82Y 10/00 |
| DE | WO 2009156898 A2 * | 12/2009 | | A61B 6/032 |
| DE | WO 2009156898 A3 * | 4/2010 | | A61B 6/032 |
| EP | 0 091 884 A2 | 10/1983 | | |
| EP | 0091884 A2 * | 10/1983 | | G01N 23/223 |
| EP | 0091884 A3 * | 8/1984 | | G01N 23/223 |
| SU | 543 289 A1 | 1/1978 | | |
| SU | 543289 A1 * | 1/1978 | | |
| WO | 01/09904 A2 | 2/2001 | | |
| WO | WO 0109904 A2 * | 2/2001 | | B82Y 10/00 |
| WO | WO 0109904 A3 * | 9/2001 | | B82Y 10/00 |
| WO | WO 0109904 A9 * | 9/2002 | | B82Y 10/00 |
| WO | 2009/156898 A2 | 12/2009 | | |

OTHER PUBLICATIONS

I.G. Grigorieva et al.; "HOPG as powerful x-ray optics", X-Ray Spectrometry, vol. 32, No. 1, Jan. 1, 2003, pp. 64-68.

Burkhard Beckhoff et al.; "New broad-hand filtering device with rectangular efficiency shape based on x-ray focusing by strongly curved HOPG crystals", Proc. SPIE 2859, Hard X-Ray/Gamma-Ray and Neutron Optics, Sensors, and Applications, Jul. 19, 1996, pp. 190-191.

International Search Report for corresponding patent application No. PCT/EP2013/072001 dated Dec. 20, 2013.

* cited by examiner

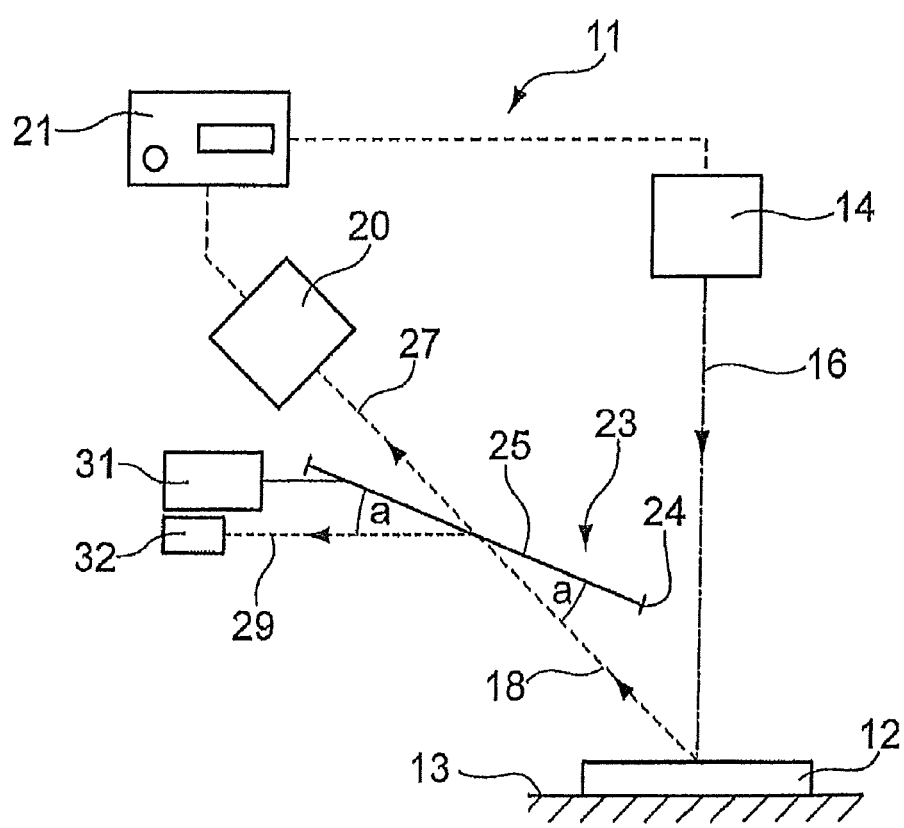

METHOD AND DEVICE FOR PERFORMING AN X-RAY FLUORESCENCE ANALYSIS

The invention relates to a method for carrying out an X-ray fluorescence analysis, as well as a device for carrying out such a method.

X-ray fluorescence analysis is generally well known. With an X-ray fluorescence analysis, a layer thickness measurement and/or a qualitative and quantitative determination of the elementary composition of a sample can be identified. The advantage lies in non-destructive measurement. For example, such an X-ray fluorescence analysis is used in the metal processing industry during the investigation and testing of alloys or testing of alloys or alloy components or layers.

In many applications, the problem exists that a signal from a metallic sub-surface, for example a signal of a ferrous component, is disruptive and the detection of individually determined alloy components or elements or layers is not able to be detected by the detector with the desired or necessary signal intensity. For one, this is because the detector is used to capacity to the greatest extent possible by this disruptive signal and, therefore, only a small proportion of the further components of the layer can be detected or this disruptive signal overlaps the further, weaker, emitted radiation.

The object of the invention is to propose a method and a device for carrying out the method, as well as a filter, whereby a simple selection of undesired wavelengths or energies is enabled in order to increase the level of measuring accuracy.

This object is solved according to the invention by a method for carrying out an X-ray fluorescence analysis in which at least one filter having at least one crystalline layer forming a filter level is introduced into the beam path of the secondary radiation, said filter acting as a band-pass filter. The filter is set at an angle $\alpha$ relative to the beam path for the reflection of at least one wavelength of the secondary radiation by Bragg reflection. A decoupled wavelength of the secondary radiation that is disrupted by Bragg reflection is detected by a second detector. The signals identified from this are forwarded to the evaluation unit. This evaluation unit can emit values or information for the adjustment device, with which the angle $\alpha$ of the filter layer of the filter is able to be adjusted relative to the secondary beam path. With this method, a selection of X-ray fluorescence lines or individual wavelengths of the secondary radiation is enabled in a simple manner by means of the filter, such that, for example, the most disruptive radiation or most disruptive rays are able to be filtered out by Bragg reflection. While measuring an alloy element or a layer of a sample body, the characteristic fluorescence lines are therefore let through by the crystalline layer of the filter, and one or more adjacent fluorescence lines or partially overlapping fluorescence lines are reflected or deflected by the filter as a result of Bragg reflection. By detecting the decoupled, disruptive radiation by means of a second detector, it can be determined whether the disruptive radiation, that is to be decoupled, is partially or fully decoupled from the secondary beam. Thus, an optimisation in the adjustment of the angular position of the filter relative to the beam path of the secondary radiation can be undertaken. By optimising the decoupling of the disruptive radiation, a reliable and exact determination of the wavelength of the secondary radiation for the alloy component(s) to be detected or the layer to be detected can be detected.

While carrying out the X-ray analysis, the filter is set at an angle $\alpha$ relative to the beam path to the component of the sample body that is to be detected, depending on the signals detected by the second detector. Due to the Bragg equations and the properties of the at least one, preferably crystalline, layer forming the filter layer, the angle $\alpha$ can be identified in order to diffract the radiation or wavelength at the filter, said radiation or wavelength not being required for the detection of the component in the sample body or even being disruptive, and letting through the wavelengths of the radiation with which the component or the layer is to be detected and determined.

The radiation that is to be filtered out or the radiation reflected at the filter is identified by a second detector, the measurement data of which is evaluated by the evaluation device. This does not only make it possible to check whether the desired radiation is filtered out, but also, after a comparison of actual and target values between the wavelength that is to be detected and/or the disruptive wavelength, enables a corresponding adjustment or control of the adjustment direction to change the angular position of the filter in order to achieve optimisation in the angular adjustment of the filter relative to the beam path of the secondary radiation, such that maximum filtering of the disruptive radiation is possible.

The object underlying the invention is furthermore solved by a device for carrying out the X-ray fluorescence analysis, in which a filter is able to be positioned in the beam path of the secondary radiation, wherein the filter has a filter layer in a filter level in order to reflect radiation that has a wavelength of the secondary radiation by Bragg reflection and to supply it to a second detector, the signals of which are able to be detected by an evaluation device. Thus, a disruptive signal can be filtered out in an optimal manner. For example, for a sample body that comprises a very thin layer on a base body made of iron, the iron represents a disruptive signal which overlaps the signals being emitted from the layer. It can also occur that, for the most part, the iron proportion is irrelevant or uninteresting for the identification. The same applies, for example, when examining a thin foil or a film that is guided along a transport roller, in particular an iron roller. Thus, the emitted radiation of the iron or transport roller can also overlap or interfere with the emitted radiation from the layer that is to be examined. Even this level of disturbance can be eliminated by the Bragg reflection at the filter. The positioning of the filter in the secondary beam path thus serves for the filtering or selection of radiation. The additional detector, which detects the at least one wavelength of the secondary radiation that has been decoupled at the filter by reflection, enables, at the same time, a comparison with the detected actual value and target value with respect to the wavelength that is to be decoupled, such that the angular position of the filter is potentially readjusted by the evaluation unit due to the output of information by the evaluation unit or due to the control of the adjustment device, such that the at least one disruptive wavelength is able to be decoupled with a maximum value.

The filter is preferably held by an adjustment device with which an adjustment of the angle $\alpha$ between the filter and the beam path is able to be controlled. This adjustment can be provided to be fixed. Alternatively, a manual or motorised adjustment can also be enabled.

The adjustment device is preferably able to be controlled by the evaluation unit, such that an exact positioning of the filter and an automatic positioning of the filter relative to the beam path of the primary and/or secondary radiation is enabled.

The filter can, in one filter level, have a filter layer made from a crystalline layer. It has astonishingly been proved that such a filter having a crystalline layer in the transmission mode is suitable for the selective reflection of individual wavelengths and moreover can be simply adjusted to the wavelength of the radiation that is to be selected.

According to a preferred embodiment of the filter, provision is made for the filter layer to be formed from the at least one crystalline layer or crystalline graphite layer as a film.

Provision is preferably made for the crystalline layer to be formed as a graphite layer. This layer of carbon atoms comprises a hexagonal lattice. Thus, depending on the spacing between the lattice planes of the layer and the angle of incidence of the radiation onto this layer, the Bragg reflection can take place for specific wavelength ranges of the primary and/or secondary radiation.

The invention and further advantageous embodiments and developments of the same are described and illustrated in greater detail below with the aid of the examples depicted in the drawings. The features that are to be gleaned from the description and the drawings may be applied individually or as a multiplicity in any combination according to the invention. Shown are:

FIG. 1 a schematic view of a device for carrying out an X-ray fluorescence analysis.

In FIG. 1, a device 11 for carrying out an X-ray fluorescence analysis in a sample body 12, such as a gold coin, is depicted schematically. This device 11 comprises an X-radiation source 14 or an X-ray tube, via which primary radiation 16 is emitted and is aimed at the sample body 12, which is held by a sample carrier 13. The sample carrier 13 can be adjusted in terms of its position and height. The primary beam 16 can, for example, be focused by a collimator that is not depicted in greater detail here. The primary beam 16 is, for example, aimed at the sample body 12 perpendicularly to the surface of the sample body 12 or at an angle deviating therefrom. Thus, X-ray fluorescence radiation is induced in the surface of the sample body 12, which is emitted from the sample body 12 as secondary radiation 16 and is detected by a detector 20 that is preferably energy-dispersive. An evaluation of the detected measurement results by the detector 20 takes place via an evaluation unit 21, which evaluates and outputs the detected data. A filter 23 is positioned in the beam path of the secondary radiation 18.

This filter 23 is formed as a transmission filter. The filter 23 comprises a filter layer 25 which lies in a filter level. The filter layer 25 is, for example, designed as a crystalline layer, in particular as a graphite layer. According to a first embodiment, only one graphite layer can form the filter layer 25. Alternatively, several layers of such graphite layers may also be provided on top of one another and may form the filter layer 25. Due to the crystalline structure of the individual graphite layers, during the transmission of the radiation through the filter 22, a wavelength is reflected or filtered out and thus selected, i.e. depending on an angle at which the filter level of the filter 23 is positioned relative to the beam path, the filter level is permeable for many wavelengths or energies of the radiation and a wavelength is diffracted. There thus takes place a selective filtering out of individual waves of the radiation.

The filter 23 can, according to a first embodiment, be constructed, for example, from a frame through which the filter layer 25 that is designed in particular as a film is held in a stretched state. Provision can also be made for this filter layer 25 designed as a film to be held in a fixed state between two frame elements. A further alternative construction of the filter 23 provides that a carrier or a carrier substrate is provided with a bore hole or a through-hole and the at least one film is adhered onto this carrier as a filter layer 25 or is applied by adhesion, wherein this at least one film or filter layer covers the bore hole or the through-hole. Alternatively, the film or filter layer 25 can also be inserted and held between two such carriers.

For the frame, aluminium or similar can, for example, be provided as the material. If the film is received between two laminar carriers or is held by one laminar carrier, this laminar carrier can, for example, be formed from a glass plate or a silicon wafer material or suchlike.

For the filter 23 arranged in the beam path of the secondary radiation 18, due to the angle of incidence of the filter level relative to the beam path, individual waves or beams are selected and diffracted at the filter layer. The Bragg scattering 29 resulting therefrom is diverted opposite the detector 20 and is detected by a second detector 32. The radiation penetrating the filter 23 then forms the radiation 27 that is to be detected by the detector 20. With this further detection of the reflected radiation, it can be monitored as to whether the angle is correctly set for the Bragg scattering, in order to reflect or decouple the desired radiation. Moreover, by slightly altering the angular position, the optimum level of adjustment of the angular position relative to the maximum reflection of the radiation that is to be selected can arise.

The angle $\alpha$ of the filter 23 relative to the beam path of the secondary radiation 18 can be adjusted manually or via a control unit by means of a schematically depicted adjustment device 31. Alternatively, the filter 23 can also be arranged in a fixed position. The angle $\alpha$ is dependent on the wavelength of the radiation that is to be absorbed, as well as the filter layer 25 or the crystalline layer(s).

An alternative device 11 to FIG. 1 differs to the extent that the filter 23 is positioned in the beam path of the primary radiation 16. Thus, a selection of the primary radiation that is to be supplied takes place, such that only filtered primary radiation 17 strikes the sample body 12.

In an alternative embodiment that is not depicted, provision can be made for a respective filter 23 to be arranged in both the beam path of the primary radiation 16 and in the beam path of the secondary radiation 18. Thus, the crystalline layers can also differ from one another in terms of their nature and/or number for the formation of the filter layer 25.

Furthermore, provision can alternatively be made for two or more filters 23 to be positioned one behind the other in a beam path for a transmission mode, said filters each being able to be controlled separately.

This device 11 for X-ray fluorescence analysis can be operated in both an energy-dispersive and wavelength-dispersive manner, wherein a corresponding adaptation of the detector 20 takes place.

To carry out the X-ray fluorescence analysis for an alloy element, in a device according to FIG. 1, the angle $\alpha$ that is to be adjusted is determined and adjusted due to the at least one crystalline filter layer 25 of the at least one filter 23, such that only the desired wavelengths of the secondary radiation 18 that are to be detected arrive at the detector 20 and the disruptive radiation is eliminated by the Bragg reflection.

Furthermore, several filters 23 may also be positioned one behind the other in the primary or secondary beam for the simultaneous filtering-out of several disruptive wavelengths.

The invention claimed is:

1. A method for carrying out an X-ray fluorescence analysis, in which a primary radiation is aimed at a sample body from an X-ray radiation source, in which a secondary radiation emitted from the sample body is detected by a detector and is evaluated by an evaluation unit, wherein at least one filter having at least one filter layer forming a filter level is introduced into the beam path of the secondary radiation and, depending on an angle α of the filter layer relative to the secondary radiation, acts as a band-pass filter and a disruptive wavelength of the secondary radiation is decoupled by Bragg reflection, the angle α of the filter layer of the filter is adjusted with an adjustment device for the reflection of at least one disruptive wavelength of the secondary radiation by Bragg reflection, and the decoupled wavelength of the secondary radiation is detected by a second detector, and the signals identified from this are forwarded to the evaluation unit.

2. The method according to claim 1, wherein the angle α of the filter layer of the filter is adjusted depending on the signals detected by the second detector.

3. The method according to claim 1, wherein the adjustment device is controlled by the evaluation unit for the adjustment of the angle α of the filter layer.

4. A device for X-ray fluorescence analysis, having an X-radiation source, the X-radiation source directs a primary radiation at a sample body located on a sample carrier and comprises a detector for the determination of secondary radiation emitted from the sample body, wherein at least one filter is positioned at least in the beam path of the secondary radiation, said filter having at least one filter layer, and at least one wavelength of the secondary radiation is reflected and decoupled by Bragg reflection at the filter, and in that a second detector is provided which detects the decoupled wavelength and forwards the signals identified therefrom to the evaluation unit.

5. The device according to claim 4, wherein the filter is received by an adjustment device, and the filter layer of the filter is controlled for the angular adjustment of the angle α relative to the incident beam path with the adjustment device.

6. The device according to claim 4, wherein the evaluation unit processes the signals from the first and/or second detector or both and the adjustment device is able to be controlled by the evaluation unit.

7. A filter for carrying out the method according to claim 1, wherein the filter has at least one filter layer which is formed from a crystalline layer.

8. The filter according to claim 7, wherein the at least one filter layer of the filter is formed as a crystalline graphite layer and has a thickness of less than 100 μm or less than 50 μm.

9. The filter according to claim 7, wherein the filter layer of the filter is formed as a film from the crystalline layer or crystalline graphite layers.

10. The filter according to claim 7, wherein the at least one filter layer is formed to be free of metallic layers.

11. The filter according to claim 7, wherein the filter layer is formed as a film, and the film is held in a stretched state by a frame.

12. The filter according to claim 7, wherein the filter layer, that is formed as a film, is provided on a plate-shaped carrier substance and is adhered or applied by adhesion to the plate-shaped carrier substance.

13. The filter according to claim 7, wherein the filter layer is a glass plate having an opening in the centre, and the filter layer, that is designed as a film, is adhered or applied by adhesion to the glass plate.

* * * * *